United States Patent [19]
Anderton et al.

[11] Patent Number: 5,994,084
[45] Date of Patent: Nov. 30, 1999

[54] MODELS OF ALZHEIMER'S DISEASE

[75] Inventors: Brian H. Anderton; Christopher C. Miller, both of London, United Kingdom

[73] Assignee: King's College London, London, United Kingdom

[21] Appl. No.: 08/596,100

[22] PCT Filed: Aug. 1, 1994

[86] PCT No.: PCT/GB94/01669

§ 371 Date: Aug. 23, 1996

§ 102(e) Date: Aug. 23, 1996

[87] PCT Pub. No.: WO95/05466

PCT Pub. Date: Feb. 23, 1995

[30] Foreign Application Priority Data

Aug. 12, 1993 [GB] United Kingdom .................... 9316727

[51] Int. Cl.⁶ .............................. G01N 33/53; C12Q 1/00; C12N 5/00; C12N 5/08
[52] U.S. Cl. ........................... 435/7.1; 435/325; 435/368; 435/4
[58] Field of Search .............................. 435/240.2, 240.1, 435/240.21, 7.21, 4, 7.1, 7.2, 172.3, 325, 368; 800/2, DIG. 1–4; 536/23.1, 23.4, 23.5; 514/2, 44

[56] References Cited

U.S. PATENT DOCUMENTS 5,162,215  11/1992  Bosselman et al. .................. 435/172.3
5,545,808   8/1996  Hew et al. .................................. 800/2

FOREIGN PATENT DOCUMENTS

WO 91/19810  12/1991  WIPO .
WO 93/02189   2/1993  WIPO .
WO 93/07280   4/1993  WIPO .

OTHER PUBLICATIONS

Houdebine, Louis–Marie. Production of pharmaceutical proteins from transgenic animals. J. of Biotech. vol. 34, pp. 269–287, 1994.
Mandelkow et al. Glycogen synthase kinase–3 and the Alzheimer–like state of microtubule–associated protein. FEBS Letters, vol. 314, No. 3, pp. 315–321, Dec. 21, 1992.
Krimpenfort et al. Generation of transgenic dairy cattle using 'in vitro' embryo production. Biotechnology, vol. 9, pp. 844–847, Sep. 1991.
Mullins et al. Transgenesis in Nonmurine species. Hypertension, vol. 22, No. 4, pp. 630–633, Oct. 1993.
Arai et al. *Proc. Natl. Acad. Sci. U.S.A.* 87:2249–2253 (1990).
Anderson et al. *J Biol Chem* 266:10131–10135 (1991).
Anderton et al. *Nature* 298:84–86 (1982).
Barcikowska et a. *Acta. Neuropathol (Berl)* 78:225–231 (1989).
Biernat et al. *EMBO J.* 11:1593–1597 (1992).
Binder et al. *J. Cell Biol.* 101:1371–1378 (1985).
Bramblett et al. *Neuron* 10:1089–1099 (1993).
Brion et al. *J. Neurochem* 60:1372–1382 (1993).
Drewes et al. *EMBO J.* 11:2131–2138 (1992).
Forss–Petter et al. *Neuron* 5:187–197 (1990).
Gallo et al. *Biochem J* 286:399–404 (1992).
Goedert et al. *EMBO J* 9:4225–4230 (1990).
Gordon et al. *Cell* 50:445–452 (1987).
Gustke et al. *FEBS Lett.* 307:199–205 (1992).
Hahn et al. *Proc. Natl. Acad. Sci. U.S.A.* 89:4387–4391 (1992).
Hanger et al. *Neurosci. Lett.* 147:58–62 (1992).
Howe et al. *Cell* 71:335–342 (1992).
Hughes et al. *Eur J Biochem* 203:305–311 (1991).
Hughes et al. *EMBO J.* 12:803–808 (1993).
Ishiguro et al. *J. Biol. Chem.* 267:10897–10901 (1992).
Jat et al. *Proc. Natl. Acad. Sci. U.S.A.* 88:5096–5100 (1991).
Julien et al. *Gene* 68:307–314(1988).
Kanai et al. *EMBO J.* 11:3953–3961(1992).
Kanai et al. *J Cell Biol* 109:1173–1184 (1989).
Kosik et al. *Cell Sci Suppl.* 15:69–74 (1991).
Lange–Carter et al. *Science* 260:315–319 (1993).
Ledesma et al. *FEBS Lett.* 308:219–224 (1992).
Liaw et al. *Proc. Natl. Acad. Sci. U.S.A.* 90:858–862 (1993).
Lichtenbrg et al. *Proc Natl. Acad. Sci. U.S.A.* 89:5384–5388 (1992).
Lovestone et al. *Curr. Opin. Neurol. Neurosurg.* 5:883–888 (1992).
McKee, A.C. *Ann. Neurol.* 30:156–165 (1991).
Miller et al. *EMBO J.* 5:269–276 (1986).
Miller et al. *Curr. Opin. Biotechnol.* 3:683–686 (1992).
Monteiro et al. *J. Cell Biol.* 111:1543–1557 (1990).
Nebreda et al. *EMBO J.* 12:1979–1986 (1993).
Posada et al. *Mol. Cell. Biol.* 13:2546–2553 (1993).
Propst et al. *Proc. Natl. Acd. Sci. U.S.A.* 87:9703–9707 (1990).
Propst et al. *J. Neuropathol. Exp. Neurol* 51:499–505 (1992).
Ruel et al. *Nature* 362:547–560 (1993).
Sternberger, N.H. and Sternberger, L.A. *Proc. Natl. Acad. Sci. U.S.A.* 80:6129–6130 (1983).
Sternbrger et al. *Proc. Natl. Acad. Sci. U.S.A.* 82:4274–4276 (1985).
Sutherland et al. *FEBS Lett.* 338:37–42 (1994).
Sutherland et al. *Biochem J* 296:15–19 (1993).
Sygowski et al. *Mol Brain Res* 20:221–228 (1994).
Vulliet et al. *J. Biol. Chem.* 267:22570–22574 (1992).
Wolozin et al. *Science* 232:648–650 (1986).
Zheng et al. *Biol. Chem.* 268:11435–1143 (1993).

*Primary Examiner*—Brian R. Stanton
*Assistant Examiner*—Deborah J. R. Clark
*Attorney, Agent, or Firm*—Leon R. Yankwich

[57] ABSTRACT

Transgenic cell and animal models for Alzheimer's disease are described. Cells of the animals and the cell models themselves comprise a recombinant DNA construct comprising a control sequence and, under the control of the control sequence, a DNA sequence encoding a kinase that is capable, directly or indirectly, of modulating the phosphorylation of the microtubule-forming protein tau. The transgenic cells and animals may be used for testing potential therapeutic agents for Alzheimer's disease.

12 Claims, 2 Drawing Sheets

FIG. 1a TRACKS 1 2 3 4 5 6

FIG. 1b TRACKS 1 2 3 4 5 6

FIG. 1c TRACKS 1 2 3 4 5 6

FIG. 1d TRACKS 1 2 3 4 5 6

FIG. 1e TRACKS 1 2 3 4 5 6

FIG. 1f TRACKS 1 2 3 4 5 6

FIG. 1g TRACKS 1 2 3 4 5 6

FIG. 1h TRACKS 1 2 3 4 5 6

FIG. 1i TRACKS 1 2 3 4 5 6

FIG. 1j TRACKS 1 2 3 4 5 6

FIG. 2a

TRACKS 1 2

FIG. 2f

TRACKS 1 2

FIG. 2b

TRACKS 1 2

FIG. 2g

TRACKS 1 2

FIG. 2c

TRACKS 1 2

FIG. 2h

TRACKS 1 2

FIG. 2d

TRACKS 1 2

FIG. 2i

TRACKS 1 2

FIG. 2e

TRACKS 1 2

FIG. 2j

TRACKS 1 2

MODELS OF ALZHEIMER'S DISEASE

The present invention relates to cell and animal models of Alzheimer's disease.

Alzheimer's disease is the most common form of senile dementia, affecting approximately 5% of individuals over 65 and 20% of those over 80. It has been estimated that there are between 2.5 and 3 million patients suffering from Alzheimer's disease in the USA and 0.6 million in the UK. These figures have been projected to increase by 20% over the next 20 years as the proportion of elderly in the population increases. As yet, there are no effective treatments for Alzheimer's disease. The development to market of a therapeutic intervention for this major human disease therefore represents a significant commercial opportunity.

Alzheimer's disease is a neurodegenerative disorder characterised histopathologically by the loss of particular groups of neurones and the appearance of two principal lesions within the brain termed neurofibrillary tangles and senile plaques (Brion, 1992).

The mechanisms that result in neuronal loss are not fully understood. The discovery of several different mutations in the gene for the amyloid precursor protein (APP) in some pedigrees with familial Alzheimer's disease has given support to the "amyloid cascade" hypothesis in which the extracellular deposition of β-amyloid is an early pathogenic event (see Hardy and Allsop, 1991; Selkoe, 1993; and Mattson et al. 1993 for reviews). While aberrant APP metabolism and deposition of β-amyloid are currently regarded as a primary pathogenic event, there is still, however, no consensus on how deposition of β-amyloid in the brain results in neurodegeneration and hence, dementia.

On the other hand, neurones containing neurofibrillary tangles almost certainly are unable to function normally and many such neurones die, as is evident from the presence of "ghost" tangles in Alzheimer brain which are the residue of dead tangle-bearing neurones.

Neurofibrillary tangles are intracellular inclusion bodies which comprise filamentous aggregates of paired helical filaments (PHF) (Lovestone and Anderton, 1992). The principal component of PHF has been shown to be tau, a microtubule-associated protein involved in stabilising the cytoskeleton and in determining neuronal shape (Kosik and Caceres, 1991). Tau is a phosphoprotein and aberrant hyperphosphorylation of tau appears to represent one, if not the, principal mechanism for its aggregation into PHF (Lovestone and Anderton, 1992). Senile plaques are composed of an extracellular fibrillar deposit of amyloid surrounded by abnormal dystrophic neurites which also contain PHF (Lovestone and Anderton, 1992). PHF pathology may also give rise to neuropil threads. Amyloid deposits are also found in the walls of cerebral blood vessels in Alzheimer's disease (Lovestone and Anderton, 1992). Amyloid fibrils in both senile plaques and cerebral blood vessels have been shown to comprise an approximately 43 residue peptide termed β-amyloid or A4. β-Amyloid is derived by proteolytic cleavage from the larger precursor protein, amyloid precursor protein (APP), a membrane-spanning glycoprotein.

Animal models of Alzheimer's disease have classically involved lesioning of particular neuronal pathways but these models are acute injury models, whereas Alzheimer's and other neurodegenerative disorders are slow and progressive (Wozniak et al., 1989; Holtzman et al., 1992; Anger, 1991; Myhrer, 1993). More recent attempts to generate animal models of Alzheimer's disease have involved transgenic manipulation of the APP (Wirak et al., 1991; Quon et al., 1991; Yamaguchi et al., 1991; Kammesheidt et al., 1992). Work has focused on APP because mutations in the APP gene have been shown to be the causative genetic defect in some familial cases of Alzheimer's disease (Mullan et al., 1992; Chartier Harlin et al., 1991; Goate et al., 1991; Murrell et al., 1991) and also because all Down's syndrome patients (trisomy of chromosome 21) develop classical Alzheimer's disease pathology by their 5th decade and this is now believed to be due to overexpression of APP by a gene dosage effect (the APP gene resides on chromosome 21) (Hardy and Allsop, 1991). In some of these transgenic APP mice, deposits of amyloid have been observed (Quon et al., 1991) but so far, no neurofibrillary tangles nor hyperphosphorylation of tau has been described.

In another approach, the proto-oncogene Mos was introduced into mice (Propst et al., 1992; Propst et al, 1990). The resulting transgenic animals showed a variety of pathological changes including neuronal and axonal degeneration in restricted areas of the brain, extensive gliosis, and inflammatory infiltrates. However, no PHF or neurofibrillary tangles were observed, and the large amount of gliosis may be involved in the neuronal degeneration.

It is becoming increasingly apparent that cognitive deficits do not occur until dystrophic neurites containing PHF and neurofibrillary tangles have developed (Barcikowska et al., 1989; Arai et al., 1990; and McKee et al., 1991). One hypothesis is that even though the primary pathogenic event in Alzheimer's disease may involve aberrant APP metabolism, the mechanism of cell death is disruption of the neuronal cytoskeleton and impairment of axonal transport caused by hyperphosphorylation of tau and its deposition as PHF (Lovestone and Anderton, 1992). The present invention is based on the appreciation that modelling neurodegenerative aspects of Alzheimer's disease is an important requirement for a useful model of the disease, in particular, animal models which generate PHF-type neurodegenerative changes and experimentally manipulated cell models in which such molecular changes occur.

The present invention provides a cell that is a model for Alzheimer's disease or for another neurodegenerative disease, which cell (i) is capable of expressing the protein tau and comprises an introduced DNA sequence encoding and capable of expressing a kinase that is capable, directly or indirectly, of modulating the phosphorylation of the protein tau or (ii) comprises an introduced DNA sequence encoding and capable of expressing the protein tau and also comprises a DNA sequence encoding and capable of expressing a kinase capable, directly or indirectly, of modulating the phosphorylation of the protein tau or iii) comprises an introduced DNA sequence encoding a control sequence, correctly integrated to allow the expression of endogenous tau and also comprises a DNA sequence encoding and capable of expressing a kinase capable, directly or indirectly, of modulating the phosphorylation of the protein tau or iv) is capable of expressing tau and comprises an introduced DNA sequence encoding a control sequence, correctly integrated to allow the expression of an endogenous kinase capable, directly or indirectly, of modulating the phosphorylation of the protein tau.

The invention also includes progeny (all subsequent generations) of a cell into which a DNA sequence has been introduced directly.

In (ii) and (iii) above, the DNA sequence encoding and capable of expressing a kinase that is capable, directly or indirectly, of modulating the phosphorylation of the protein tau may be endogenous, may have been introduced or may be introduced, for example, further copies of an endogenous gene may be introduced to bring about over-production of the chosen kinase.

A cell according to the present invention, preferably in the form of a cell line that may be cultured continuously, is a recombinant cell that may be obtained by manipulation of cells using conventional techniques of recombinant DNA technology. Mammalian cells are preferred as the base cells for manipulation to incorporate DNA sequences in accordance with the present invention. Some cells, for example, neuroblastomas, are capable of expressing the protein tau; others, for example, fibroblasts, do not normally express tau. If a cell does not normally express tau, then the cell should be adapted to express tau by introduction of a DNA sequence encoding tau under the control of appropriate regulatory DNA sequences, for example the human cytomegalavirus major intermediate early promoter/enhancer region (CMV promoter). The resulting DNA sequence may be considered a "recombinant" DNA sequence or "transgene". Splicing and polyadenylation sequences may also be included within the transgene, for example the Simian virus 40 (SV40) early splice and polyadenylation region so as to stabilise the messenger RNA produced from the transgene. Alternatively, expression of an endogenous tau gene may be induced by the correct integration of appropriate control sequences adjacent to the tau gene. Alternatively, a primary culture, which can be cultured for a limited period, may be obtained from a transgenic animal of the present invention. Such cultures may be immortalised. Further details regarding recombinant cells according to the present invention are given below.

The term "introduced DNA sequence" is used herein to denote a DNA sequence that has been introduced into a cell and which may or may not be incorporated into the genome. The DNA sequence may be a sequence that is not endogenous to the chosen type of cell, that is endogenous but is not normally expressed by that cell or that is endogenous and is normally expressed but of which over-expression is desired. The DNA sequence may be introduced by any suitable transfection technique including electroporation, calcium phosphate precipitation, lipofection or the use of viral infection methods such as the use of retroviruses. The sequence may have been introduced directly into the cell or may have been introduced into an earlier generation of the cell.

The present invention also provides a transgenic animal, especially a transgenic rodent, that is a model for Alzheimer's disease or for another neurodegenerative disease, cells of which animal comprise a recombinant DNA construct comprising (a) a control sequence that directs expression to the nervous system and (b) in the correct reading frame and under the control of the control sequence, a DNA sequence encoding a kinase that is capable, directly or indirectly, of modulating the phosphorylation of the microtubule-forming protein tau.

The present invention includes animals into which a construct has been introduced directly and also progeny (all subsequent generations) of those animals, which progeny retain the construct.

A cell or animal that is a model for Alzheimer's disease or another neurodegenerative disease is one which models one or more aspects of Alzheimer's disease or another neurodegenerative disease. The cell or animal need not model all aspects of the disease.

The use of a neurone-specific control sequence, for example, derived from a gene encoding a neurone-specific protein, for example, a neurofilament light chain gene or heavy chain gene, drives expression of the recombinant kinase in the cells of the central nervous system, in particular the brain. Alternatively, there may be used a control sequence that is not neurone-specific but that is capable of driving expression inter alia in the nervous system. An example is the murine sarcoma virus long terminal repeat promoter which, although somewhat promiscuous, has been shown to drive high level expression in the brain.

As indicated above, one of the many possible factors involved in Alzheimer's disease is hyperphosphorylation of tau. This may be caused by an abnormality of some sort in the activity of kinases and phosphatases which regulate the phosphorylation status of tau. Kinases involved directly in phosphorylation of tau have been identified by the incubation of recombinant tau produced in $E.\ coli$ with ATP and candidate kinases. Such in vitro studies have revealed that mitogen activated kinases (also known as microtubule-associated kinases and abbreviated herein to "MAP" kinases), for example, p42 MAP kinase, and also glycogen synthase kinase $3\alpha$ and $3\beta$ (GSK-$3\alpha$ and GSK-$3\beta$), cdc2 kinase, cdK5 kinase and one or more brain proline-directed kinases are capable of phosphorylating tau on at least some residues which are phosphorylated in PHF-tau (Biernat et al., 1992; Drewes et al., 1992; Gustke et al., 1992; Hanger et al., 1992; Ishiguro et al., 1992; Ledesma et al., 1992; Lichtenberg Kraag et al., 1992; Mandelkow et al., 1992; Vulliet et al., 1992). All of the above kinases are therefore candidates for modulating the phosphorylation status of tau in vivo.

Incubation of a candidate kinase with recombinant tau (produced in vitro) and ATP, followed by analysis of the phosphorylation status of the tau, is one method which may be used to ascertain whether the candidate kinase is capable of directly phosphorylating tau. An example of such a method is described in detail in Example 1, Part B.

Several of the kinases that may be involved in the hyperphosphorylation of tau themselves require activation. Activation of MAP kinases has been shown to require phosphorylation on both tyrosine and threonine residues by a MAP kinase kinase (MEK) (Lange-Carter et al., 1993; Zheng and Guan, 1993). MEK itself requires phosphorylation on serine and threonine residues for activity which argues for the presence of MEK kinase(s). Recently, the products of the proto-oncogenes c-Raf-1, mos and a newly isolated MEK kinase (MEKk) bearing homology to the yeast Stell and Byr2 genes have been shown to phosphorylate and activate MEK (Lange-Carter et al., 1993; Zheng and Guan, 1993; Liaw et al., 1993; Nebreda and Hunt, 1993; Posada et al., 1993; Howe et al., 1992). c-Raf-1 lies on the signal transduction cascade from tyrosine kinase receptors and is itself positively regulated by phosphorylation on tyrosine and serine residues. However, the viral v-Raf or N-terminally truncated c-Raf is constitutively active. MEKk lies on the alternate signal transduction pathway from G-protein coupled receptors and transfection experiments have indicated that its activity may be regulated at least partly at the transcriptional level. Thus MAP kinase can be constitutively activated by expression of v-Raf/truncated c-Raf isoforms or by overproduction of MEKk or by mutant consitutive MEKk isoforms. Such kinases are therefore involved indirectly in the modulation of the phosphorylation of tau and may be used in the present invention. If desired, a variant of the assay described in Example 1 Part B (involving both the kinase requiring activation and the kinase(s) required to bring about that activation) may be used to assess the suitability of a candidate kinase that acts indirectly.

The corresponding mechanisms by which GSK-3α and GSK-3β are activated are not fully understood but that of GSK-3β is best characterised. Phosphorylation on tyrosine 216 is required for activity of GSK-3β although GSK-3β is tyrosine phosphorylated in tissues under resting conditions (Hughes et al., 1993). A further level of regulation involves phosphorylation on serine and/or threonine residues by certain protein kinase C (PKC) isotypes which results in inactivation of GSK-3β. Since GSK-3β is tyrosine phosphorylated in resting conditions, overproduction of GSK-3β by introducing one or more further copies of the GSK-3β gene will lead to a cellular increase in the level of tyrosine phosphorylated but PKC unphosphorylated sites and, hence, activated species and thereby an increase in activity of the enzyme. A further level of regulation involves phosphorylation of serine 9 in human GSK-3β. Phosphorylation at this site down-regulates activity of that enzyme. Analogous considerations apply to GSK-3α.

Modelling of Alzheimer's disease PHF-type hyperphosphorylation of tau may therefore be achieved by genetic manipulations using those kinases involved directly or indirectly in the phosphorylation of tau. A construct is, for example, designed to express one or more of v-Raf, mos, a truncated c-Raf-1 and MEKk (indirect activation via MAP kinase), GSK-3α and GSK-3β (direct activation) in transgenic animal neurones or in cultured cells capable of expressing tau.

As pointed out above, a desired level of GSK-3β or GSK-3α activity may be obtained by manipulations designed to introduce further copies of the gene in cells already containing the gene and hence to achieve direct over-production of that protein. Similarly, over-production of other kinases that may be involved directly in the phosphorylation of tau, for example, mitogen activated kinases, and cdc2 kinase and brain proline-directed kinases may be achieved by introducing extra copies of the gene into a cell or an animal. However, as the activation of at least some of the above kinases appears to be the result of an enzyme cascade, an amplified effect may be achieved by introducing into a cell or an animal DNA encoding an enzyme from higher position in the cascade. Accordingly, in the case of mitogen activated kinase it may be preferable to introduce DNA encoding a MAP kinase kinase, for example, MEK, and especially preferable to introduce DNA encoding an enzyme capable of activating a MAP kinase kinase, for example, v-Raf, mos, a truncated c-Raf-1 or MEKk. The DNA encoding the enzyme is preferably introduced such that the enzyme is over-produced.

We have found that the introduction of expressible copies of the glycogen synthase kinase-3β gene or glycogen synthase kinase-3α gene into cultured cells that are capable of expressing tau is particularly effective in achieving PHF-type hyperphosphorylation of tau. The cells may either be inherently capable of expressing tau or may be induced to express tau by the introduction of appropriate control sequences or by the introduction of expressible DNA sequences encoding tau. Multiple copies of the GSK-3β or GSK-3α gene may be introduced in order to bring about over-expression of the protein.

For example, in cultured mammalian COS7 cells, in cells with introduced DNA encoding tau, tau was phosphorylated by co-transfection with DNA encoding glycogen synthase kinase-3β (GSK-3β) so that it resembled Alzheimer's disease PHF-tau as assessed by reactivity with antibodies which recognise PHF-tau from Alzheimer's diseased adult brain but not human tau from normal adult brain and also as assessed by retarded migration on sodium dodecyl sulphate polyacrylamide gel electrophoresis (SDS-PAGE). Co-transfection with GSK-3α also gave the same results.

Accordingly, in the various embodiments of the present invention, the kinase that is capable, directly or indirectly, of modulating the phosphorylation of the microtubule-forming protein tau is preferably a glycogen synthase kinase, especially glycogen synthase kinase-3α or glycogen synthase kinase-3β.

Methods for introducing DNA into cells, for example, involving the use of cloning and expression vectors are very well known, see for example, Sambrook J., Fritsch E. F., Maniatis T. Molecular cloning: A laboratory manual, Cold Spring Harbor 1989.

Methods of introducing DNA into animals to produce functional transgenic animals are also well established, see for example, Hogan B., Costantini, F., Lacy, E., Manipulating the mouse embryo: A laboratory manual, Cold Spring Harbor, 1986. Rodents, in particular mice and rats, are particularly useful in the present case as there are well-established behavioural tests for such animals.

Control systems that drive expression to neurones are known. They include both control systems that are neurone-specific and control systems that are more or less promiscuous but that induce high levels of expression in neurones. Depending on the nature of the construct used in the production of the transgenic animal and, in particular, the control elements, the desired kinase may be expressed in all neurones or only in restricted subsets of neurones of transgenic animals. Neurone-specific control systems, that drive expression to neuronal cell types in general, are known. They may be derived from genes encoding neurone-specific proteins. Such systems may be used to bring about expression of the desired kinase in neurones. For example, if it is desired that the kinase should be expressed in all neuronal cell types of transgenic rodents, then the mouse or human neurofilament light (NF-L) gene in which cloning sites have been engineered into the MRNA encoding leader sequences or the mouse neurofilament heavy (NF-H) gene, cloned as a KpnI to SalI fragment (Julien et al., 1988) may be used to drive expression. In such a case, sequences encoding the kinase may be cloned within the unique MRNA leader sequences (a NotI site in the case of NF-H) (see Julien et al., 1988 for gene structure).

Other sequences which may assist in directing high level expression of the gene may also be included in such a transgene. These include a polyadenylation signal sequence such as that from the Simian virus 40 or additional intron sequences such as intron 7 from the mouse Ren-1D gene.

An example of a control sequence active in various tissues but that induces a high level of expression in neurones is the murine sarcoma virus long terminal repeat promoter. Further examples of control sequences are the promoter region of the neurone-specific enolase gene (Forss-Petter, S et al., 1990) and the human Thy-1 gene regulatory elements known to direct expression to the nervous system (Gordon, J. W et al., 1987).

The cholinergic system is particularly affected in Alzheimer's disease and so expression of kinases in this particular cell type only, for example via the choline acetyl transferase gene promoter, provides a model for cholinergic deficits. The choline acetyl transferase gene has been partially cloned from pig, human and rat (see for example, Hahn et al, 1992).

As an alternative to producing recombinant cells by direct genetic manipulation, recombinant cells, especially neurones, may be obtained from transgenic animals and cultured in vitro. Primary cells can be maintained in culture for a limited time only. However, it is now possible to immortalise animal cells and to maintain them in culture indefinitely (see, for example, Jat et al. 1991).

Crucial for the development of therapeutic agents for Alzheimer's disease are cell and animal based models which mimic aspects of the pathology, i.e., model wholly or partly, neurofibrillary tangle and/or senile plaque pathology. Such experimental models are required for a variety of applications. A recombinant cell or transgenic animal model of the present invention may be utilised to unravel the molecular cascade of events leading to nerve cell death in Alzheimer's disease such that therapeutic intervention points may be identified. Furthermore, the models may be used in screening to identify and assess the efficacy of potential therapeutic agents, for example, in preventing hyperphosphorylation of tau. Preventing such hyperphosphorylation may hinder or prevent the formation of neurofibrillary tangles and hence delay the onset and/or the progression of Alzheimer's disease or even prevent the disease.

Methods for screening potential therapeutic agents using cell lines and also using animals are very well established. Recombinant cell lines and transgenic animals of the present invention may be used analogously.

Cell-based models are generally used in early stage screening. Screening assays may, for example, involve immunoassays. In one example antibodies, for example, monoclonal antibodies, may be produced against phophorylated and non-phosphorylated tau epitopes. Examples of such antibodies are: antibody TP70, which is a polyclonal antibody to tau raised in rabbits, which antibody recognises all tau isoforms so far studied including PHF-tau (our unpublished observations); antibodies 8D8, RT97, 121.5, BF10 (Miller et al., 1986), AT8 (Bierat et al., 1992), SMI31, SMI34, SMI310 (Sternberger et al., 1985; Sternberger and Sternberger, 1983) and ALZ-50 (Wolozin et al., 1986), which are all mouse monoclonal antibodies which recognise PHF-tau but react less strongly or do not react at all with tau found in normal adult human brain; and antibody Tau-1, which is a mouse monoclonal which recognises normal but not PHF-tau (Binder et al., 1985).

Screening may be carried out as follows: Recombinant cells of the present invention or primary or immortalised cell cultures derived from transgenic animals of the present invention are incubated with a potential therapeutic agent. The cells are then incubated with tau-specific antibodies and with hyperphosphorylated tau-specific antibodies and the extent of binding of the antibodies indicates the extent to which hyperphosphorylation has occurred. The less hyperphosphorylation, the more effective the candidate therapeutic agent. Binding of the antibody to the cells may be detected directly, if the antibody is labelled with a detectable label, or indirectly, for example, with a labelled anti-species antibody. The label may be a radio-label or a fluorescent label or, especially, an enzyme label. The screening assay is preferably an ELISA (enzyme-linked immunosorbent assay). Such assays can be carried out on a large scale using microtitre plates and automated or semi-automated apparatus.

Accordingly, the invention provides a screening assay kit comprising:

i) recombinant cells of the present invention or primary or immortalised cell cultures derived from transgenic animals of the present invention ii) an antibody, preferably a monoclonal antibody, capable of binding selectively to phoshorylated tau, and optionally iii) an antibody, preferably a monoclonal antibody, capable of binding selectively to unhyperphoshorylated (normal) tau.

Advantageously the screening assay is an enzyme-linked immunosorbent assay.

Transgenic animals themselves may be used to test the efficacy and safety of interesting compounds. The effect of such compounds, for example, on the production of neurofibrillary tangles in test animals, may be determined by carrying out various investigations on the animals after sacrifice. Furthermore, the ability to apply behavioural testing to the transgenic animals enables cognitive function to be monitored following treatment with potential therapeutic agents.

The recombinant cell lines and transgenic animals of the present invention may also serve as models for other neurodegenerative disorders in which there is evidence of abnormal cytoskeletal protein phosphorylation; these conditions include Parkinson's disease, motor neurone disease (also known as amyotrophic lateral sclerosis), senile dementia of the Lewy body type (SDLT), and stroke. Accordingly, the recombinant cell lines and transgenic animals of the present invention may be used for the study of such conditions and screening of therapeutic agents for such conditions.

Accordingly, the present invention provides a method of testing a potential therapeutic agent using target cells in vitro, characterized in that a recombinant cell of the present invention is used as the target cell. The present invention also provides a method of testing a potential therapeutic agent for a specified condition comprising using an animal model for that condition, characterized in that the condition is Alzheimer's disease or another neurodegenerative disease and the animal model is a transgenic animal of the present invention. The potential therapeutic agents are especially for the prevention and/or treatment of Alzheimer's disease, Parkinson's disease, motor neurone disease, senile dementia of the Lewy body type (SDLT), or stroke.

As indicated above, construction of transgenic animals, for example, rodents, and the construction of cell lines expressing kinases believed to modulate tau phosphorylation status may be achieved by placing cDNA or genomic sequences encoding these kinases under the control of homologous or heterologous gene controlling or promoter sequences by using cloning vectors, for example, plasmids (eg Bluescript, Stratagene).

In the case of recombinant cells, the kinase transgene may be introduced into and expressed by cells that already produce tau naturally, for example, neuronal cells, for example, SHSY5Y cells. Alternatively, the kinase transgene may be introduced into and expressed in cells that do not normally express tau, for example, fibroblasts. In the latter case the cells are manipulated to express tau by the introduction of DNA, generally cDNA or a genomic sequence, that encodes tau, expression of the tau transgene being placed under the control of a heterologous or homologous gene controlling promoter sequence, generally using a cloning vector, for example, a plasmid. The DNA sequence encoding tau and that encoding the kinase may be incorporated in the same construct or may each be in a separate construct.

In one embodiment designed to drive expression to neuronal cell types of transgenic animals, a 7 kb mutated murine neurofilament light chain (NF-L) gene in which cloning sites have been engineered into the mRNA encoding leader sequences (Monteiro et al., 1990) may be used to drive expression. Here, the DNA sequence encoding the kinase may be cloned into the BamH1 site within the NF-L leader. Polyadenylation and splicing sequences are then provided by the downstream NF-L structural gene. The NF-L gene has been shown to drive expression to neuronal cell types and so this particular transgene is useful for expressing the kinases in all neuronal cell types of transgenic animals.

In this particular example, the unique BamH1 site in the NF-L mRNA leader sequence is used to insert a DNA sequence encoding the desired kinase, for example, a GSK-3β protein. The kinase-encoding sequence is inserted into the BamH1 site in one of two ways, firstly, by engineering BamH1 compatible DNA sequences onto the ends of the kinase-encoding DNA sequences and then, following cleavage with the restriction enzyme BamH1, ligating those sequences into the BamH1 cloning site and cloning into E. coli.

Alternatively, following restriction with BamH1, the BamH1 cloning site in the NF-L sequence is rendered blunt-ended by incubation with a DNA polymerase, for example, T4 polymerase or the Klenow fragment of E. coli polymerase 1 and appropriate deoxyribonucleoside triphosphates in appropriate buffers and the kinase-encoding sequence is rendered blunt-ended in a similar fashion. The kinase-encoding sequence is then ligated into the blunt-ended NF-L mRNA encoding leader sequence and cloned in E. coli.

kinase. Here an EcoR1 to Sma1 fragment containing the MSV promoter (Propst et al., 1990) is cloned into the EcoR1 and SmaI sites of pSVK3 (Pharmacia). DNA encoding GSK-3β, for example, a cDNA GSK-3β, is then cloned into the unique XhOI site of this plasmid by making the DNA ends blunt as described above with T4 polymerase. The vector sequences are removed by digestion with EcoR1 and BglII prior to construction of transgenic mice.

Human GSK-3β cDNA, which is preferably used in the production of constructs, may be utilised in a wild type form or, alternatively, following modification of a wild type gene. One such possible modification is to add at the 3' end of the cDNA, DNA sequences which encode an epitope recognised by an antibody since this will enable transgenic GSK-3β to be distinguished from endogenous mouse GSK-3β. For example, sequences encoding an additional 11 amino acids encoding a hemaglutinin (HA) marker may be engineered towards the end of the coding part of the cDNA. The latter part of the coding region of the GSK-3β cDNA would then read:

```
aactccactagtTACCCATACGATGTTCCAGATTACGCAAGCTTGggtggtcccaactag  (SEQ ID NO:4)
```

(Marker sequences in capitals)

In a further example, the mouse NF-H gene (cloned as a KpnI to SalI fragment) (see Julien et al., 1988 for gene structure) is used to drive expression of the kinase to neurones; a sequence encoding the kinase is inserted within the unique Not1 site within the mRNA leader sequence of the mouse NF-H gene and cloned into E. coli. In one example, DNA, for example, cDNA, encoding human GSK-3β is first cloned into a plasmid vector such that Not-1 sites flank the GSK-3β insert. The kinase-encoding DNA is then excised with Not1 and recloned into the Not1 site of the NF-H gene.

In a modification, other sequences which may assist in directing high level expression of the gene are also included in the transgene. These include intron 7 sequences from the mouse Ren-1D gene to give additional splicing signals and/or a polyadenylation signal sequence from the Simian virus 40. Here, intron 7 of the mouse Ren-1D gene can be amplified by the polymerase chain reaction (PCR) using primers (1) and (2) or (3) and (4)

| | | |
|---|---|---|
| (1) | CGTCGGCCGTAGGCCCTGCCTCCCAGGTC | (SEQ ID NO:1) |
| (2) | CGTCGGCCGCAGTTGATCATGCAAGCCCTG | (SEQ ID NO:2) |
| (3) | CGTCGGCCGTAGGCCCTGCCTCCCAGGTC | (SEQ ID NO:1) |
| (4) | CGTCGGCCGCGGCAATAAAAAGACAGAATAAA | (SEQ ID NO:3) |
| | ACGCACGGGTGTTGGGTCGTTTGTTAG | |
| | TTGATCATGCAAGCCCTG | |

Primer (4) includes the SV40 polyadenylation signal. Since the primers include Eagl restriction sites which have complementary overhangs to Not1 sites at their 5' ends, the PCR product is cleaved with Eag1 and cloned into the Not1 site of the NF-H gene. When cloned in the correct orientation, this produces a unique Not1 site into which the kinase is cloned. In these NF-H/GSK-3β transgenes, the vector sequences are removed by digestion with Kpn1 and Sal1 prior to construction of transgenic mice. The MSV promoter may be used to drive expression of the selected Additionally, site-directed mutagenesis may be used to substitute an alanine residue for a serine residue at codon 9 of GSK-3β since phosphorylation of this residue is known to down-regulate activity of the kinase. Such a mutant GSK-3β is predicted to be hyperactive.

Analogous transgenes to those described above may be constructed using DNA encoding a different gene, for example, GSK-3α, in place of that encoding GSK-3β.

Other regulatory sequences known to be capable of driving expression specifically to neurones in transgenic mice include the promoter region of the neurone-specific enolase gene (Forss-Petter, S. et al. 1990) and the human Thy-1 gene regulatory elements (Gordon, J. W et al., 1987). Any such neurone-specific control sequence may be used with any desired kinase according to the present invention, for example, to achieve overexpression of GSK-3α or GSK-3β.

It will, however, be appreciated that not every transgene will function optimally in every cell type and animal type. Work of a routine nature may be required to establish the best kinase, tau isoform, control sequence and combination of kinase, tau isoform and control sequence for any particular cell type or animal type. If both a tau transgene and a kinase transgene are to be incorporated in a cell or animal, they may have different optimal control sequences.

Further selectivity of expression may be achieved by using controlling promoter sequences from genes expressed in particular subsets of neurones. The cholinergic system is particularly affected in Alzheimer's disease. The controlling sequences from the choline acetyl transferase gene may be used to drive expression to cholinergic cells of transgenic animals, thus providing a particularly useful model for Alzheimer's disease. The construction of such kinase expression vectors utilises standard techniques of molecular biology (see, for example, Sambrook J., Fritsch E. F., Maniatis T., Molecular cloning: A laboratory manual, Cold Spring Harbor 1989).

A variety of methods for constructing transgenic animals have been described including gene transfer into embryonic stem (ES) cells, retroviral infection of early embryos and pronuclear microinjection (Hogan B., Costantini, F., Lacy, E., Manipulating the mouse embryo: A laboratory manual, Cold Spring Harbor, 1986). Both transgenic rats and mice have been created by the pronuclear microinjection route, which is particularly appropriate for the experiments described here. Manipulated embryos are then transferred into the reproductive tracts of pseudopregnant females. Such techniques may also be used for the production of other transgenic mammals.

For example, where the pronuclear microinjection route is chosen for the production of transgenic mice, a typical strategy is to obtain embryos from juvenile C57B1/6×CBA/ca F1 female mice which have been caused to superovulate by intraperitoneal injection with follicle stimulating hormone and then 46 hours later with human chorionic gonadotropin and which have then been mated with fertile male C57B1/6×CBA/ca F1 mice. These embryos are cultured in M2 or M16 medium (Hogan et al., 1986) and injected with the required DNA as a solution, preferably of approximately 1–2 ng per $\mu$l. Once injected, the embryos are reimplanted into the oviducts of foster mothers which have been made pseudopregnant by mating with vasectomised male mice.

Approximately one in five of the mice born will be transgenic and those transgenic mice may be identified by Southern analysis of DNA prepared from tail biopsies.

As indicated above, cultured cell lines that express both tau and the desired kinase may be derived by isolating primary neuronal cultures from the transgenic animals and, if desired, immortalising the cells or alternatively, by introducing a kinase expression transgene into a cell line expressing tau. Tau expressing cells may be neuroblastomas or alternatively, cell lines genetically engineered to express tau via the introduction of tau-expressing transgenes. It will be appreciated that when recombinant cells are produced directly, that is by the introduction of transgenes into cell lines, it is not necessary to use a neurone-specific control sequence.

A variety of methods have been described for introducing DNA transgenes into cultured mammalian cells by transfection and include electroporation, calcium phosphate precipitation, lipofection and viral infection methods such as the use of retroviruses (see, Sambrook J., Fritsch E. F., Maniatis T., Molecular cloning: A laboratory manual, Cold Spring Harbor 1989).

The present invention provides a method of producing a transgenic non-human animal, especially a transgenic mammal, more especially a rodent, that is a model for Alzheimer's disease or for another neurodegenerative disease, which comprises incorporating in cells of a non-human animal a DNA construct comprising (a) a control sequence that directs expression to the nervous system and (b) in the correct reading frame and under the control of the control sequence, a DNA sequence encoding a kinase that is capable, directly or indirectly, of modulating the phosphorylation of the microtubule-forming protein tau.

The DNA construct is preferably incorporated in the genome of the animal.

The present invention further provides a DNA construct comprising a DNA sequence encoding a kinase capable of modulating the phosphorylation of the microtubule-forming protein tau and also comprising control sequences such that the kinase is overexpressed.

The present invention also provides a DNA construct comprising (i) a control sequence that directs expression to the nervous system and (ii) in the correct reading frame and under the control of the control sequence, a DNA sequence encoding a kinase that is capable, directly or indirectly, of modulating the phosphorylation of the microtubule-forming protein tau.

Such a DNA construct of the invention may also comprise a DNA sequence encoding the microtubule-forming protein tau, in the correct reading frame and preferably also under the control of the control sequence The following figures illustrate the Examples described in detail below:

FIGS. 1a to 1j illustrate Example 1, Part A and FIGS. 2a to 2j illustrate Example 1, Part B. The figures are as follows:

The blots were probed with a number of different antibodies and the following Figures show the results of probing with the stated antibodies:

| | |
|---|---|
| FIGS. 1a and 2a | TP70 |
| FIGS. 1b and 2b | Tau 1 |
| FIGS. 1c and 2c | AT8 |
| FIGS. 1d and 2d | RT97 |
| FIGS. 1e and 2e | 8D8 |
| FIGS. 1f and 2f | 121.5 |
| FIGS. 1g and 2g | BF10 |
| FIGS. 1h and 2h | SMI310 |
| FIGS. 1i and 2i | SMI31 |
| FIGS. 1j and 2j | SM134 |

The following non-limiting Examples illustrate the present invention.

EXAMPLE 1

Part A

In cultured mammalian COS7 cells, transfected tau was phosphorylated by co-transfection with glycogen synthase kinase-3$\beta$ (GSK-3$\beta$) or glycogen synthase kinase-3$\alpha$ (GSK-3$\alpha$) so that it resembled Alzheimer's disease PHF tau as assessed by reactivity with antibodies that are capable of binding selectively to PHF tau, that is to say, antibodies that bind to PHF tau and that have little or no cross-reactivity with human tau from normal adult brain, and also as assessed by retarded migration on sodium dodecyl sulphate polyacrylamide gel electrophoresis (SDS-PAGE).

Human GSK-3$\beta$, or human GSK-3$\alpha$, and a human tau isoform were transiently overexpressed in mammalian COS7 cells by introducing expression vectors designed to express GSK-3$\beta$, GSK-3$\alpha$ and tau. To do so, DNA sequences encoding the human GSK-3$\beta$ complementary DNA (cDNA), or the human GSK-3$\alpha$ cDNA, as an EcoR1 fragment was ligated into the mammalian expression vector pMT-2, which vector contains the Simian virus 40 origin of replication (see Sambrook et al. 1989) at the EcoR1 site and checked for correct orientation. Likewise, DNA sequences encoding a human tau cDNA isoform, human tau 1N4R (a tau containing four tubulin binding repeats and one N-terminal insert) also as an EcoR1 fragment was cloned into PSGS (Strategene Ltd.).

Tau expression plasmids alone or in combination with either GSK-3$\alpha$ or GSK-3$\beta$ expression plasmids were introduced by transfection into COS7 cells using an electroporator. To do so COS-7 cells were cultured, in the usual way, in Dulbecco's modification of Eagle's medium (DMEM) containing 10% (v/v) foetal calf serum supplemented with 2 mM glutamine, 100 U/ml penicillin and 100 μg/ml streptomycin. Cells were harvested by trypsinisation and resuspended in Optimem medium (Life Sciences, Strathclyde, UK) at a concentration of $2 \times 10^7$ cells per ml. 15 μg, in 30 μl of sterile ultrapure water, of each plasmid DNA used was introduced by electroporation using a BioRad electroporator operating at 0.22 kV, 960 μF in a 0.4 cm path length electroporation chamber containing $10^7$ cells in 0.4 ml. Following electroporation, cells were immediately resuspended in DMEM containing foetal calf serum, as above, and plated onto 64 cm² Petri dishes. The cells were allowed to adhere either for 48 hours prior to harvesting for analysis or, in experiments involving serum starvation, for 40 hours, after which serum was removed and the cells incubated for a further 8 hours. Routinely, half of the transfected cells from each experiment was processed for analyses of tau phosphorylation by Western blotting and half for assays of kinase activities.

Tau Assays

For analysis of tau phosphorylation, cells were harvested following chilling by scraping them into 1.5 ml of phosphate buffered saline, they were then pelleted by centrifugation, at 800 g(av) for 10 minutes and resuspended in 120 ml of Mes-sodium chloride buffer (Mes is 2-[N-Morpholino] ethane sulphonic acid) comprising 100 mM Mes pH6.5, 0.5 mM $MgCl_2$, 1 mM ethylene glycol-bis (β-aminoethyl ether) N,N,N',N'-tetraacetic acid (EGTA) and 1 M NaCl supplemented with 2 mM dithiothreitol (DTT), 17.5 μg/ml leupeptin, 175 μg/ml phenylmethylsulphonylfluoride (PMSF), 20 μg/ml aprotinin, 50 mM sodium fluoride and 0.1 mM sodium vanadate. To isolate tau, the harvested cells were heated in a boiling water bath for 5 minutes and the insoluble fraction removed by centrifugation in a microfuge for 15 minutes. The supernatant containing tau was prepared for SDS-PAGE by addition of SDS-PAGE sample buffer comprising 1% SDS in 0.0625 M Tris/HCl buffer (Tris is tris[hydroxymethyl]aminomethane) pH6.8 and DTT (as a reducing agent) and analysed by Western blotting using the antibodies described below.

GSK-3 assay.

The assay described is unable to distinguish between GSK-3β and GSK-3α activity.

Cells were homogenised in glass Dounce homogenisers (Sturgill et al. 1991) in a homogenising buffer of 25 mM Tris HCl buffer pH 7.7 containing 2 mM EGTA, 40 mM sodium p-nitrophenyl phosphate, 1 mM sodium vanadate and protease inhibitors (1 mM benzamidine, 2 μg/ml aprotinin, 5 μg/ml leupeptin, 1 μg/ml pepstatin A and 50 μg/ml PMSF) and centrifuged at 4° C. for 10 minutes at 10,000 g. The supernatant was stored in aliquots at −70° C. Protein concentrations were determined with the Pierce bicinchoninic acid reagent as described by the manufacturers (Pierce & Warriner (UK) Ltd., Chester, Cheshire, CH1 4EF). After diluting in homogenising buffer to normalise for protein, extracts were batch purified by binding to phenyl-Sepharose (Pharmacia), (adapted from the method of Anderson et al. 1991). Aliquots of 10.75 ml containing 75 to 400 μg protein were mixed with 0.1 ml phenyl-Sepharose beads for 10 to 20 minutes at 4° C., centrifuged and washed twice with 0.75 ml of extraction buffer/ethylene glycol (9:1 by volume). GSK-3α or GSK-3β was absorbed to the resin and was eluted by addition of 0.1 ml of cold ethylene glycol to the packed resin and mixing for 10 minutes.

5 μl of extract was incubated at 30° C. for 15 to 30 mins with 8 μM substrate peptide (GS-1) (Woodgett, 1989) in 25 mM Tris HCl buffer pH7.5 containing 10 mM $MgCl_2$, 1 mM EGTA, 1 mM DTT, 50 μM and 1 μCi [(γ-$^{32}$P] ATP, 5 mg/ml bovine serum albumin and 10 g/μl heparin in a volume of 20 μl. Reactions were terminated by addition of 20 μl of ice cold 5 mM ATP in 20% trichloroacetic acid. After centrifugation for 6 minutes in a microfuge, 25 μl of the supernatant was pipetted onto P81 paper. The substrate peptide (GS-1) had been phosphorylated with casein kinase II and non-phosphorylated GS-1 was used as a control. Pieces of P81 paper were washed 5 times in 75 mM phosphoric acid and immersed in water for Cerenkov counting.

Tau, GSK-3β and GSK-3α proteins from the transfected cells were analysed by SDS-PAGE and Western blotting. Proteins were separated on 10% SDS-PAGE gel, and blotted onto nitrocellulose membranes (Schleicher and Schuell, Anderman UK) using a BioRad semi-dry Trans-Blot blotter and probed with antibodies which detect GSK-3β and antibodies which distinguish between non-phosphorylated and phosphorylated (PHF-tau) epitopes.

The GSK-3β antibody was a polyclonal antibody raised in rabbits to purify GSK-3β and was obtained from Dr. Jim Woodgett (Ontario Cancer Research Institute/St. Magaret's Hospital, Toronto).

Ten different antibodies were used to carry out the Western blots for the analysis of tau. TP70 is a polyclonal antibody raised in rabbits to a synthetic tau peptide (Brion et al. 1993). Tau 1 was obtained from Dr L Binder, SMI antibodies from Sternberger monoclonals (Affinity Research Products Ltd, UK) and AT8 from Innogenetics, Ghent, Belgium. Monoclonal antibodies 121.5, BF10, RT97, 8D8, SMI310, SM131 and SM134 are all selective for PHF-tau (Anderton et al. 1982; Miller et al. 1986; Sternberger et al., 1985; Sternberger and Sternberger, 1983).

To visualise antibody reactivity a biotin/streptavidin/alkaline phosphatase detection system with appropriate anti-mouse or anti-rabbit immunoglobulins was used (Amersham International UK, Biorad UK).

Controls

As well as transfecting COS7 cells with the tau isoforms alone, tau from normal human brains, from Alzheimer's diseased brain and recombinant tau 1N4R produced in *E. coli* were analysed. Normal human brain tau was prepared from frozen adult human brains as described (Brion et al., 1991a) and PHF-tau prepared from histologically confirmed Alzheimer's disease brain frozen at autopsy as described (Brion et al., 1991b). Recombinant tau 1N4R was produced in *E. coli* as described (Goedert and Jakes, 1990).

As may be seen from FIG. 1 and Table 1, following transfection with tau alone, reactivity of tau can be detected with antibodies TP70 and Tau-1 but little or no reactivity is observed with the PHF-tau antibodies. However, when tau is transfected with either GSK-3β or GSK-3α, reactivity is detected with all of the PHF-tau-selective antibodies. In addition, the tau proteins from the cells co-transfected with GSK-3β or GSK-3α have a reduced mobility on SDS-page, which is characteristic of PHF-tau prepared from Alzheimer's diseased brain. The GSK-3β analysis shows a substantial increase in the amount of GSK-3β compared to non-transfected cells.

Table 1 shows the reactivity of each sample with the antibodies listed below. A series of "+" signs is used to denote reactivity with an antibody. The use of the signs is semi-quantitative in that a greater number of signs indicates a higher reactivity with an antibody, for example, "++" indicates higher reactivity with the antibody than does "+".

This information is to assist in the interpretation of the Western blots of FIGS. 1a to j.

FIGS. 1a–j are Western blots of:
Track 1: Tau isolated from a normal human brain
Track 2: Recombinant tau 1N4R produced in E. coli
Track 3: Tau extracted from COS7 cells transfected with tau alone
Track 4: Tau extracted from COS7 cells co-transfected with tau and GSK-3β
Track 5: Tau extracted from COS7 cells co-transfected with tau and GSK-3α
Track 6: PHF-tau isolated from an Alzheimer's disease brain 1a is probed with antibody TP70
1b is probed with antibody Tau 1
1c is probed with antibody AT8
1d is probed with antibody RT97
1e is probed with antibody 8D8
1f is probed with antibody 121.5
1g is probed with antibody BF10
1h is probed with antibody SMI310
1i is probed with antibody SMI31
1j is probed with antibody SMI34

Figure 1A:
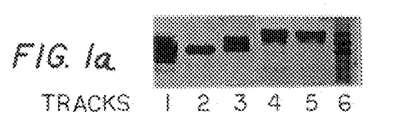
FIGS. 1a to 1j, show Western blot analyses of proteins prepared in Example 1. Those proteins are: tau isolated from serum-starved COS7 cells transiently transfected with Tau 1N4R either alone, or in combination with human GSK3$\beta$ or human GSK3$\alpha$.
Figure 1B:
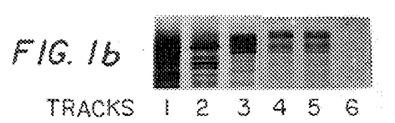
Figure 1C:
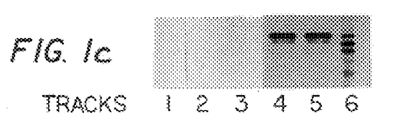
Figure 1D:
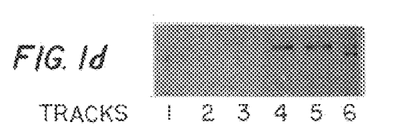
Figure 1E:
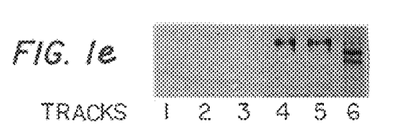
Figure 1F:
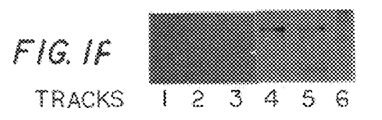
Figure 1G:
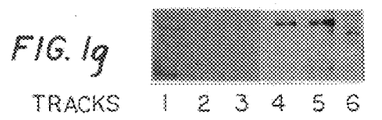
Figure 1H:
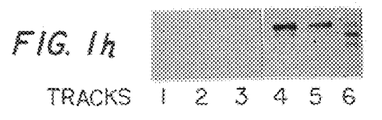
Figure 1I:
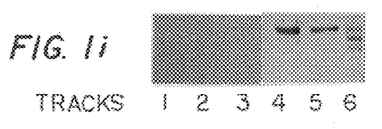
Figure 1J:
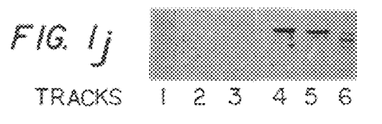

Antibodies AT8, RT97, 8D8, 121.5, BF10, SMI310, SMI31 and SMI34 are all selective for PHF tau but in our hands will sometimes weakly label tau from normal human brain (see for example track 1 in FIG. 1g).

Tau isolated from serum-starved COS7 cells transfected with a CDNA encoding Tau1N4R (Track 3) migrated as 2 to 3 major bands of immunoreactivity following Western blotting with a polyclonal antiserum to tau (TP70), FIG. 1a, which detects both normal and PHF-tau. The tau migrated in similar positions to tau isolated from normal human brain (Track 1) with the fastest migrating species running close to unphosphorylated recombinant human Tau 1N4R produced in E. coli (Track 2). Tau from these cells also reacted strongly with antibody Tau 1, FIG. 1b, which recognises tau from normal human brain but not PHF-tau. However, Tau 1 also reacted with species that migrated faster than recombinant tau, which may be a consequence of some form of post-translational modification to a proportion of the cellular tau that increases the gel migration rate; this species may be proteolysed since it was unreactive with antibody TP70 which was raised to a C-terminal peptide of tau.

In contrast to the labelling with antibodies TP70 and Tau 1, tau isolated from the COS7 cells transfected with tau alone failed to react, or reacted very weakly with antibodies AT8, RT97, 8D8, 121.5, BF10, SMI310, SMI31 and SMI34 which are all selective for PHF-tau (FIGS. 1c–j, Track 3). Interestingly however, this weak reactivity was with species that had a reduced migration rate on the gels (see for example FIG. 1i track 3) which indicates that a small proportion of the tau in these transfected COS7 cells may be phosphorylated at some PHF-tau epitopes. The locations of the epitopes for these antibodies, where known, are listed in Table 1.

Tau isolated from transfected COS7 cells grown continuously in foetal bovine serum-containing medium migrated in an identical fashion and displayed the same antigenic profile (data not shown) indicating that the presence or absence of growth factors provided by serum has little effect on tau phosphorylation.

The phosphorylation status of transfected tau has now been studied in a number of different mammalian cell types (Bramblett et al. 1993; Gallo et al. 1992; Kanai et al. 1989; Kanai et al. 1992; Sygowski et al. 1994). A proportion of transfected tau has been shown to be phosphorylated at PHF-tau epitopes $Ser^{396}$ (the 8D8 epitope (Hanger et al. 1992)) and $Ser^{199}/Ser^{202}$ (the Tau 1 epitope) in 3T3 cells (Sygowski et al. 1994) and likewise, $Ser^{396}$ is phosphorylated in CHO cells but in this cell type, phosphorylation appears to be dependent upon the number of tubulin-binding domains present in the transfected tau (Bramblett et al. 1993). COS7 cells were therefore transfected with a tau isoform containing only three tubulin binding repeats and one N-terminal insert (Tau 1N3R). The cells were cultured and analysed as described above. Similar results were observed to those with Tau 1N4R, see Table 1.

The observed differences in the phosphorylation of transfected tau between COS cells, 3T3 cells and CHO cells may be due to inherent differences in tau kinase/phosphatase activities in the different cell types or possibly because these earlier studies investigated tau phosphorylation in stably transfected cells whereas we have studied transiently transfected cells. Whatever the reason(s), the absence of PHF-tau epitopes in the majority of the tau in these transiently transfected COS7 cells provided us with a valuable cell system to assay the effects of tau kinases.

Modulation of GSK-3β and GSK-3α activity was carried out as described above. Both of these enzymes are active in quiescent cells (Hughes et al. 1993) which we confirmed in serum-starved COS cells (Table 1). However, co-transfection of tau with a cDNA encoding human GSK-3β induced a 5 to 6-fold increase in GSK-3 activity in these cells (Table 1). Tau isolated from GSK-3β co-transfected cells (Track 4) migrated differently to tau isolated from tau only transfected COS7 cells. Instead of the 2 to 3 major bands of immunoreactivity discerned with the polyclonal tau antibody TP70 and which migrate in a similar position to tau isolated from normal human brain, as described above, we observed a pronounced reduction in electrophoretic mobility of the tau such that one/two species now migrated in a similar position to the slowest migrating species in a PHF-tau preparation (FIG. 1a, Track 6). Furthermore, these tau species reacted strongly with monoclonal antibodies AT8, RT97, 8D8 121.5, BF10, SMI310, SMI31 and SMI34 which all recognise phosphorylated epitopes present in PHF-tau, but did not react with antibody Tau 1 which does not label PHF-tau (FIGS. 1b–j, track 4). The absence of labelling of these slower migrating species with antibody Tau 1 was demonstrated by processing one half of a blot with Tau 1 and the other half with antibody AT8 (data not shown). However, Tau 1 still labelled, albeit more weakly, some faster migrating tau species in a manner similar but not identical to control cells demonstrating that there is some heterogeneity in the phosphorylation status of tau in these GSK-3β co-transfected cells. The failure of TP70 to react strongly with these faster migrating species recognised by Tau 1 may also be due to as yet, uncharacterised changes at the C-terminus of the tau since TP70 was raised against a C-terminal peptide of tau.

Tau isolated from cells co-transfected with both the tau vector and with a CDNA encoding GSK-3α migrated in an identical fashion to cells co-transfected with tau and GSK-3β and displayed the same antigenic profile (FIGS. 1a–j, track 5).

It has been suggested that the number of tubulin binding repeat domains may in some way influence the phosphorylation status of tau in transfected cells (Bramblett et al. 1993). GSK-3β-induced phosphorylation of tau in COS7 cells expressing a tau isoform with one N-terminal insert but only three tubulin binding repeat domains (Tau 1N3R) was therefore carried out and analysed. The cells were cultured and analysed as described above. This isoform of tau was affected by elevation of GSK-3β activity as much as was Tau 1N4R (original data not shown but see Table 1 for Tau 1N4R result) indicating that in COS cells, the number of tubulin binding repeat domains has little or no effect on GSK-3-mediated phosphorylation.

This example demonstrates that in cultured mammalian cells, upregulating the activity of GSK-3α and GSK-3β induces phosphorylation of transfected tau so that it appears indistinguishable from PHF-tau as assayed by reactivity with nine PHF-tau selective monoclonal antibodies and also that this phosphorylation gives rise to a reduction in the electrophoretic mobility of the tau that is characteristic of PHF-tau. Indeed, the 5 to 6-fold increase in GSK-3 activity in the cells co-transfected with GSK-3β cDNAs compared to cells transfected with tau alone, demonstrates that increased enzyme protein levels result in greater enzymatic activity and this is consistent with a direct phosphorylation of tau by GSK-3.

Part B

In vitro phosphorylation of tau

The following protocol is described in terms of in vitro phosphorylation of tau using GSK-3B. The protocol may be carried out, mutatis mutandis, using any other kinase capable or thought to be capable of phosphorylating tau either directly ot indirectly. The protocol may therefore be used to test candidate kinases for use in the present invention.

Protocol

Recombinant human Tau1N4R was produced in *E.coli* (Goedert and Jakes, 1990). Rat GSK-33 was purified from Sf9 cells infected with a recombinant baculovirus (Hughes et al. 1991). For phosphorylation, 1 mg of tau was incubated with GSK-33 at 30° C. in 20 mM HEPES buffer pH 7.5 containing 5 mM $MgCl_2$, 0.5 mM DTT, 1 mM PMSF, 10 μM leupeptin, 10 μM pepstatin, 1.5 μM aprotinin, 5 μM okadaic acid and 10 μM sodium orthovanadate. The reaction was started by the addition of ATP (final concentration 1 mM) and terminated after 24 hours by heating the samples to 100° C. for 5 minutes. Controls contained GSK-3β which had been heat-inactivated prior to incubation. Samples were prepared for SDS-PAGE by addition of SDS-PAGE sample buffer and analysed by Western blotting, as described in Part A above.

Results

FIG. 2 shows Western blots analyses of proteins prepared in the above experiment. FIGS. 2a–j are Western blots of:

Track 1: Tau extracted from control incubations

Track 2: Tau extracted following phosphorylation with GSK3B.

Figure 2A:
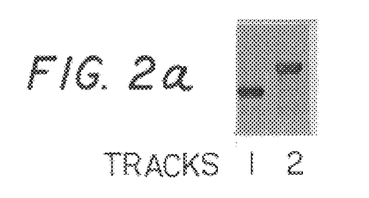
FIGS. 2a to 2j, show Western blot analyses of proteins prepared in the experiments of Example 2, which demonstrate in vitro phosphorylation of tau with purified GSK3$\beta$.

2a is probed with antibody TP70

Figure 2B:
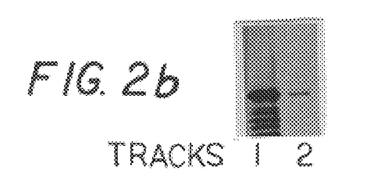

2b is probed with antibody Tau 1

Figure 2C:
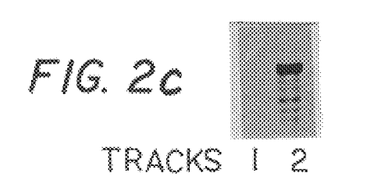

2c is probed with antibody AT8

Figure 2D:
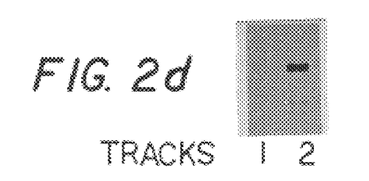

2d is probed with antibody RT97

Figure 2E:
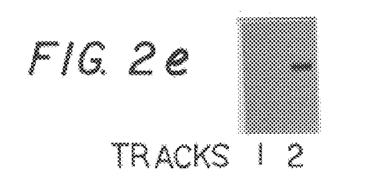

2e is probed with antibody 8D8

Figure 2F:
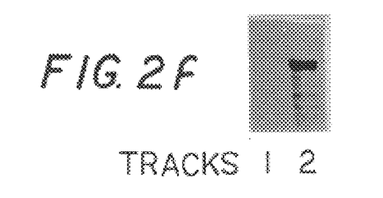

2f is probed with antibody 121.5

Figure 2G:
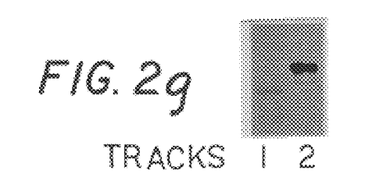

2g is probed with antibody BF10

Figure 2H:
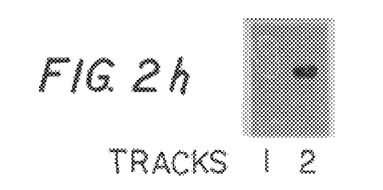

2h is probed with antibody SMI310

Figure 2I:
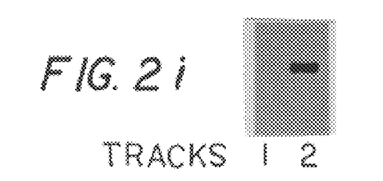

2i is probed with antibody SMI31

Figure 2J:
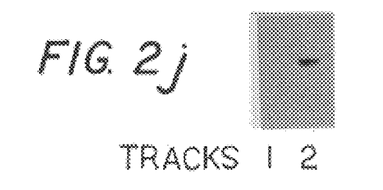

2j is probed with antibody SMI34

Discussion of results using GSK-3β

GSK-3α and GSK-3β have already been shown to phosphorylate recombinant tau produced in *E. coli* so as to generate a number of PHF-tau epitopes (Mandelkow et al. 1992; Hanger et al. 1992). In the experiments described here, GSK-3B generated epitopes for antibodies AT8, RT97, 8D8, 121.5, BF10, SMI310, SMI31 and SMI34 and induced a decrease in labelling with antibody Tau 1. Hence, the results observed in COS7 cells co-transfected with GSK-3β complement those obtained in vitro.

EXAMPLE 2

The pronuclear microinjection route was used in experiments to produce transgenic mice.

Juvenile C57B1/6×CBA/ca F1 female mice were caused to superovulate by intraperitoneal injection with follicle stimulating hormone and then 46 hours later, with human chorionic gonadotropin. The mice were then mated with fertile male C57B1/6×CBA/ca F1 mice. Embryos were collected and cultured in M2 or M16 medium (Hogan et al., 1986) and injected with DNA solution, see below, at approximately 1–2 ng per μl in 5 mM Tris-HCl buffer, pH 7.5 and 0.1 mM EDTA. Once injected, the embryos were reimplanted into the oviducts of foster mothers which had been made pseudo-pregnant by mating with vasectomised male mice. For details of micro-injection techniques see Hogan et al. Manipulating the mouse embryo: A laboratory manual, Cold Spring Harbour, 1986.

The DNA solutions which were used were as follows:

(1) The MSV promoter driving expression of wild type human GSK-3β tagged with a hemaglutinin epitope (see page 18 of the reference for details of the hemaglutinin marker), and (2) a similarly tagged GSK-3β transgene in which serine 9 (of the wild type GSK-3β DNA fragment) was mutated to alanine in order to attempt to increase GSK-3β activity (see above).

Baby mice have been born and their progress is being monitored. It is usual in such micro-injection experiments that about one in five animals born is transgenic, that is one in five animals has the DNA construct incorporated in its DNA. These animals may be identified by Southern blot analysis of samples, for example, of tail biopsies.

Animals which are born transgenic are termed founder transgenics. These animals will generally breed true, that is they pass the transgene on to 50% of their offspring (they are heterozygous at this stage).

Several different founders will usually be generated in such an experiment since the transgene may be incorporated in different places in the animals' DNA. The expression of the transgene can therefore vary between different transgenic lines harboring the same DNA construct. For example, if a transgene, under the control of neurone specific regulatory elements, were by chance to integrate within the mouse insulin gene then the animal would have a mixture of regulatory elements, pancreatic and neurone specific and at this locus. This might create some form of hybrid expression pattern in the animal.

In order to determine the expression pattern of the transgene and to study the effect of the expression tha brain and other organs of the animals can be studied by Western blotting and immunocytochemistry/histology. Such methods are well known and documented.

In the above described experiments the GSK transgene comprises a hemaglutin epitope marker. This extra DNA sequence encodes a peptide which can be easily recognised by an appropriate monoclonal antibody. In this way transgenic GSK protein may be easily detected in expression studies. The phosphorylation of tau in such animals may be studied using the techniques and antibodies described above in Example 1.

Kinase activities and immunoreactivity of tau with a panel of polyclonal and monoclonal antibodies.

| Source of tau COS cells transfect. with:- | Enzyme activity GSK-3 | TP70 C-term. peptide | Tau. 1* $Ser_{199}$ $Ser_{202}$ unphos. | AT8 $Ser_{202}$ phos. | RT97 phos. in N-term. insert | 8D8 $Ser_{396}$ phos. | 121.5 Phos depend. unknown | BF10 Phos depend. unknown | SMI310 Phos depend. unknown | SMI31 $Ser_{396}$ $Ser_{404}$ phos. | SMI34 Phos. depend. conform. |
|---|---|---|---|---|---|---|---|---|---|---|---|
| Tau 1N4R | 1 | +++ | +++ | − | − | − | − | − | − | (+) | − |
| Tau 1N3R | ND | +++ | +++ | − | − | − | − | − | − | − | − |
| Tau 1N4R + GSK-3β | 5–6 | +++ | − | +++ | + | ++ | + | ++ | ++ | ++ | ++ |
| Tau 1N3R + GSK-3β | ND | +++ | − | +++ | + | ++ | + | ++ | ++ | ++ | ++ |
| Tau 1N4R + GSK-3α | ND | +++ | − | +++ | + | ++ | + | ++ | ++ | ++ | ++ |
| Control human tau | NA | +++ | +++ | − | − | − | − | (+) | − | − | − |
| PHF-tau | NA | +++ | − | +++ | + | ++ | + | + | ++ | ++ | ++ |

Notes:
ND—not determined; NA—not applicable;
GSK-3 activities are expressed as relative activities;
*ve symbols in the transfected cell columns refer to labelling of the slower migrating species recognised by PHF-tau reactive antibodies.

BIBLIOGRAPHY

Anger, W. K. (1991) Neurotoxicology. 12, 403–413.
Arai, H. et al. (1990) Proc. Natl. Acad. Sci. U.S.A. 87, 2249–2253.
Anderton et al. (1982) Nature 298, 84–86.
Anderton et al. (1991) J Biol Chem 266, 10131–10135.
Barcikowska, M. et al. (1989) Acta. Neuropathol (Berl) 78, 225–231.
Biernat, J. et al. (1992) EMBO J. 11, 1593–1597.
Binder, L. I. et al. (1985) J. Cell Biol. 101, 1371–1378.
Bramblett, G. T. et al. (1993) Neuron 10, 1089–1099.
Brion, J.-P. et al. (1991a) Biochem. J. 273, 127–133.
Brion, J.-P. et al. (1991b) Biochem. J. 279, 831–836.
Brion, J.-P. (1992) Biochim. Biophys. Acta Protein Struct. Mol. Enzymol. 1160, 134–142.
Brion, J.-P. et al. (1993) J Neurochem 60, 1372–1382.
Chartier Harlin, et al. (1991) Nature 353, 844–846.
Drewes, G. et al. (1992) EMBO J. 11, 2131–2138.
Forss-Petter, S. et al. (1990) Neuron 5, 187–197.
Gallo J-M, et al., (1992) Biochem J 286, 399–404.
Goate, A. et al. (1991) Nature 349, 704–706.
Goedert and Jakes (1990) EMBO J 9, 4225–4230.
Gordon, J. W. et al. (1987) Cell 50, 445–452.
Gustke, N. et al. (1992) FEBS Lett. 307, 199–205.
Hahn et al. (1992) Proc. Natl. Acad. Sci. U.S.A. 89, 4387–4391.
Hanger, D. P. et al. (1992) Neurosci. Lett. 147, 58–62.
Hardy, J. and Allsop, D. (1991) Trends Pharmacol. Sci. 12, 383–388.
Hogan et al. (1986) Manipulating the mouse embryo: A laboratory manual, Cold Spring Harbor.
Holtzman, D. M. et al. (1992) Proc. Natl. Acad. Sci. U.S.A. 89, 1383–1387.
Howe, L. R. et al. (1992) Cell 71, 335–342.
Hughes, K. et al. (1991) Eur J Biochem 203, 305–311.
Hughes, K. et al. (1993) EMBO J. 12, 803–808.
Ishiguro, K. et al. (1992) J. Biol. Chem. 267, 10897–10901.
Jat et al. (1991) Proc. Natl. Acd. Sci. U.S.A. 88, 5096–5100.
Julien et al. (1988) Gene 68, 307–314.
Kammesheidt, A. et al. (1992) Proc. Natl. Acad. Sci. USA 89, 10857–10861.
Kanai, Y. et al. (1992) EMBO J 11, 3953–3961.
Kanai, Y. et al. (1989) J Cell Biol 109, 1173–1184.
Kosik, K. S. and Caceres, A. (1991) J. Cell Sci. Suppl. 15, 69–74.
Lange-Carter, C. A. et al. (1993) Science 260, 315–319.
Ledesma, M.D. et al. (1992) FEBS Lett. 308, 218–224.
Liaw, G.-J. et al. (1993) Proc. Natl. Acad. Sci. USA 90, 858–862.
Lichtenberg Kraag, B. et al. (1992) Proc. Natl. Acad. Sci. U.S.A. 89, 5384–5388.
Lovestone, S. and Anderton, B. H. (1992) Curr. Opin. Neurol. Neurosurg. 5, 883–888.
Mandelkow, E.-M. et al. (1992) FEBS Lett. 314, 315–321.
Mattson M. P. et al. (1993) Trends Neurosci 16, 409–414.
McKee, A. C. et al. (1991) Ann. Neurol. 30, 156–165.
Miller, C. C. J. et al. (1986) EMBO J. 5, 269–276.
Miller, C. C. J. and Anderton, B. H. (1992) Curr. Opin. Biotechnol. 3, 683–686.
Monteiro, M. J. et al. (1990) J. Cell Biol. 111, 1543–1557.
Mullan, M. et al. (1992) Nature Genet. 1, 345–347.
Murrell, J. et al. (1991) Science 254, 97–99.
Myhrer, T. (1993) Neurosci. Biobehav. Rev. 17, 195–202.
Nebreda, A. R. and Hunt, T. (1993) EMBO J. 12, 1979–1986.
Posada, J. et al. (1993) Mol. Cell. Biol. 13, 2546–2553.
Propst, F. et al. (1990) Proc. Natl. Acad. Sci. U.S.A. 87, 9703–9707.
Propst, F. et al. (1992) J. Neuropathol. Exp. Neurol. 51, 499–505.
Quon, D. et al. (1991) Nature 352, 239–241.
Ruel, L. et al. (1993) Nature 362, 547–560.
Sambrook, J. et al. (1989) Molecular Cloning: A laboratory manual, Cold Spring Harbor, Cold Spring Harbor Laboratory Press.
Selkoe, D. (1993) Trends Neurosci 16, 403–409.
Sternberger, N. H. & Sternberger, L. A. (1983) Proc. Natl. Acad. Sci. USA 80,6126–6130.
Sternberger, N. H. et al. (1985) Proc. Natl. Acad. Sci. USA 82,4274–4276.
Sturgill et al. (1991) Methods Enzymol 200, 342–351.

Sutherland, C. and Cohen P. (1994) FEBS Lett 338, 37–42.
Sutherland, C. et al. (1993) Biochem J 296, 15–19.
Sygowski, L. A. et al. (1994), Mol Brain Res 20, 221–228.
Vulliet, R. et al. (1992) J. Biol. Chem. 267, 22570–22574.
Wirak, D. O. et al. (1991) Science 253, 323–325.
Wolozin, B. L. et al. (1986) Science 232, 648–650.
Woodgett (1989) Anal Biochem 180, 237–241.
Wozniak, D. F. et al. (1989) Neuroscience 32, 685–700.
Yamaguchi, F. et al. (1991) Neuroreport 2, 781–784.
Zheng, C.-F. and Guan, K.-L. (1993) J. Biol. Chem. 268, 11435–11439.

We claim:

1. An isolated cell selected from the group consisting of:
   (i) a cell that expresses the protein tau and comprises an introduced DNA sequence encoding a kinase that modulates the phosphorylation of the protein tau, wherein said cell expresses said kinase;
   (ii) a cell that comprises a DNA sequence that encodes a kinase that modulates the phosphorylation of the protein tau, and also comprises an introduced DNA sequence that encodes the protein tau, wherein said cell expresses said protein tau and said kinase;
   (iii) a cell that comprises a DNA sequence that encodes a kinase that modulates the phosphorylation of the protein tau, wherein said cell expresses said kinase, said cell also comprising an introduced DNA sequence encoding a promoter correctly integrated to direct the expression of endogenous tau;
   (iv) a cell that expresses the protein tau and comprises an introduced DNA sequence encoding a promoter, correctly integrated to direct the expression of an endogenous kinase that modulates the phosphorylation of the protein tau; and,
   (v) a cell that comprises an introduced DNA sequence encoding the protein tau and an introduced DNA sequence encoding a kinase that modulates the phosphorylation of the protein tau, wherein said cell expresses the protein tau and said kinase, said DNA sequences having been incorporated into said cell either as separate constructs or the same construct;
   wherein said kinase is selected from the group consisting of glycogen synthase kinase-3α and glycogen synthase kinase-3β, and wherein said isolated cell when cultured exhibits hyperphosphorylation of tau and/or neurofibrillary tangles characteristic of a neurodegenerative disorder.

2. A cell as claimed in claim 1, wherein the cell may be cultured continuously.

3. A cell as claimed in claim 1, wherein the cell is a neuroblastoma cell.

4. A cell as claimed in claim 1, which comprises at least one further kinase that modulates the phosphorylation of the protein tau, said further kinase being selected from the group consisting of a mitogen activated kinase, a glycogen synthase kinase, cdc2 kinase, cdK5 kinase or a brain proline-directed kinase, a mitogen activated kinase kinase, v-Raf, mos, truncated c-Raf-1, a MEK kinase, and a mutated and constitutively active MEK kinase.

5. A cell as claimed in claim 1, wherein said cell comprises two or more copies of an introduced DNA sequence encoding said kinase.

6. A method of testing a potential therapeutic agent using target cells in vitro, comprising;
   1) providing a cell as claimed in claim 1, said cell exhibiting hyperphosphorylation of the protein tau,
   2) incubating said potential therapeutic agent with said cell, and
   3) subsequently measuring the extent to which said protein tau is phosphorylated, wherein a reduction in phosphorylation relative to that observed in a cell of claim 1 not incubated with said potential therapeutic agent indicates that said agent is a potential therapeutic.

7. A method as claimed in claim 6, wherein the potential therapeutic agent is incubated with the target cells and then immunoassay is used to test for the presence of hyperphosphorylated tau.

8. A method as claimed in claim 7, wherein the immunoassay used is an enzyme-linked immunosorbent assay (ELISA).

9. A method as claimed in claim 6 wherein the potential therapeutic agent is a potential therapeutic agent for the prevention or treatment of Alzheimer's disease, Parkinson's disease, motor neurone disease, senile dementia of the Lewy body type (SDLT), or stroke.

10. A screening assay kit comprising:
    (i) cells as claimed in claim 1 and
    (ii) an antibody that binds selectively to phosphorylated tau, and optionally
    (iii) an antibody that binds selectively to unhyperphosphorylated tau.

11. A screening assay kit as claimed in claim 10, wherein the screening assay is an enzyme-linked immunosorbent assay.

12. A method as claimed in claim 8, wherein said potential therapeutic agent is a potential therapeutic agent for the prevention or treatment of Alzheimer's disease, Parkinson's disease, motor neurone disease, senile dementia of the Lewy body type (SDLT), or stroke.

* * * * *

```
SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH:  29 base pairs
        (B) TYPE: nucleic acid
        (C) STRANDEDNESS: single
        (D) TOPOLOGY:  linear (ii) MOLECULE TYPE: cDNA (iii) HYPOTHETICAL: no (iv) ANTI-SENSE: no (vi) ORIGINAL SOURCE:
        (A) ORGANISM: Mus muscaris (xi) SEQUENCE DESCRIPTION: SEQ ID NO: 1:

CGTCGGCCGT AGGCCCTGCC TCCCAGGTC                                      29

(2) INFORMATION FOR SEQ ID NO: 2:

(i) SEQUENCE CHARACTERISTICS:
        (A) LENGTH:   30 base pairs
        (B) TYPE: nucleic acid
        (C) STRANDEDNESS: single
        (D) TOPOLOGY:  linear (ii) MOLECULE TYPE: cDNA (iii) HYPOTHETICAL: no (iv) ANTI-SENSE: no (xi) SEQUENCE DESCRIPTION: SEQ ID NO: 2:

CGTCGGCCGC AGTTGATCAT GCAAGCCCTG                                     30

(2) INFORMATION FOR SEQ ID NO: 3:

(i) SEQUENCE CHARACTERISTICS:
        (A) LENGTH: 77 base pairs
        (B) TYPE: nucleic acid
        (C) STRANDEDNESS: single
        (D) TOPOLOGY:  linear (ii) MOLECULE TYPE: cDNA (iii) HYPOTHETICAL: no (iv) ANTI-SENSE: no (vi) ORIGINAL SOURCE: Mus muscaris (xi) SEQUENCE DESCRIPTION: SEQ ID NO: 3:

CGTCGGCCGC GGCAATAAAA AGACAGAATA AAACGCACGG GTGTTGGGTC               50

GTTTGTTAGT TGATCATGCA AGCCCTG                                        77
```

```
(2) INFORMATION FOR SEQ ID NO: 4:

(i) SEQUENCE CHARACTERISTICS:
        (A) LENGTH: 60 base pairs
        (B) TYPE: nucleic acid
        (C) STRANDEDNESS: single
        (D) TOPOLOGY:  linear (ii) MOLECULE TYPE: cDNA (iii) HYPOTHETICAL: no (iv) ANTI-SENSE: no (vi) ORIGINAL SOURCE: Homo sapiens (xi) SEQUENCE DESCRIPTION: SEQ ID NO: 4:

AACTCCACTA GTTACCCATA CGATGTTCCA GATTACGCAA GCTTGGGTGG          50

TCCCAACTAG                                                     60
```